United States Patent
Jandacek et al.

(10) Patent No.: US 7,695,971 B2
(45) Date of Patent: Apr. 13, 2010

(54) USE OF NON-ABSORBABLE FAT IN DETERMINING DIETARY FAT ABSORPTION

(75) Inventors: Ronald James Jandacek, Cincinnati, OH (US); Patrick Tso, Loveland, OH (US); James E. Heubi, Cincinnati, OH (US)

(73) Assignees: Children's Hospital Medical Center, Cincinnati, OH (US); University of Cincinnati, Cincinnati, OH (US)

( * ) Notice: Subject to any disclaimer, the term of this patent is extended or adjusted under 35 U.S.C. 154(b) by 625 days.

(21) Appl. No.: 10/567,143

(22) PCT Filed: Aug. 5, 2004

(86) PCT No.: PCT/US2004/025350
§ 371 (c)(1), (2), (4) Date: Jun. 21, 2006

(87) PCT Pub. No.: WO2005/015201
PCT Pub. Date: Feb. 17, 2005

(65) Prior Publication Data
US 2006/0258009 A1 Nov. 16, 2006

Related U.S. Application Data

(60) Provisional application No. 60/481,187, filed on Aug. 6, 2003.

(51) Int. Cl.
*G01N 33/92* (2006.01)
*G01N 33/02* (2006.01)
*G01N 37/00* (2006.01)

(52) U.S. Cl. .............. 436/71; 436/20; 436/56; 436/94; 436/164

(58) Field of Classification Search ........... 436/8, 436/13, 71, 94, 164, 20, 56; 128/898
See application file for complete search history.

(56) References Cited

U.S. PATENT DOCUMENTS

| | | | |
|---|---|---|---|
| 3,600,186 A * | 8/1971 | Mattson et al | 426/611 |
| 3,716,631 A | 2/1973 | Steggerda et al. | |
| 3,818,089 A | 6/1974 | Bayley et al. | |
| 4,005,196 A * | 1/1977 | Jandacek et al. | 514/23 |
| 5,017,398 A * | 5/1991 | Jandacek et al. | 426/603 |
| 5,085,884 A * | 2/1992 | Young et al. | 426/611 |
| 5,466,434 A | 11/1995 | Kyle | |
| 5,504,202 A | 4/1996 | Hutchison | |
| 6,006,754 A | 12/1999 | Janghorbani et al. | |
| 6,821,545 B2 * | 11/2004 | Bernhardt et al. | 426/611 |
| 7,241,468 B2 * | 7/2007 | Naber et al. | 426/611 |

OTHER PUBLICATIONS

DAHER, G. C. et al., Olestra Ingestion and Dietary Fat Absorption in Humans, J. Nutr. (1997), 127: 1694S-1698S.
HOVING, J. et al., Estimation of fat absorption from single fecal specimens using $^{131}$I-triolein and $^{75}$Se-triether. A study in rats with and without induced steatorrhea, *Gastroenterology*, (1977) 72:406-412.
JANDACEK et al., A Novel, Noninvasive Method for the Measurement of Intestinal Fat Absorption, *Gastroenterology* (2004), 127:139-144.
JANDACEK et al., Effects of partial replacement of dietary fat by olestra on dietary cholesterol absorption in man, *Metabolism*, (Aug. 1990) vol. 39 No. 8 pp. 848-852.
JANDACEK et al., Physical properties of pure sucrose octaesters, *Chem and Physics of Lipids* (1978), vol. 22 pp. 163-176.
FALLAT, R. W. et al.; Short term study of sucrose polyester a nonabsorbable fat-like material as a dietary agent for lowering plasma cholesterol $^{1-3}$; *The American Journal of Clinical Nutrition*, vol. 29, Nov. 1976, pp. 1204-1215.

* cited by examiner

*Primary Examiner*—Maureen M Wallenhorst
(74) *Attorney, Agent, or Firm*—Hasse & Nesbitt LLC; Daniel F. Nesbitt

(57) ABSTRACT

The use of sucrose polyester containing behenate fatty acid chains as a non-absorbable fat marker to determine total dietary fat absorption by the digestive tract of a subject. A test food for use in measuring fat absorption contains a non-absorbable fat and a dietary fat. The method is useful for diagnostic testing for diagnosing malabsorption of dietary fat by the digestive tract of the subject, and impairment of dietary fat digestion in the subject.

19 Claims, 5 Drawing Sheets

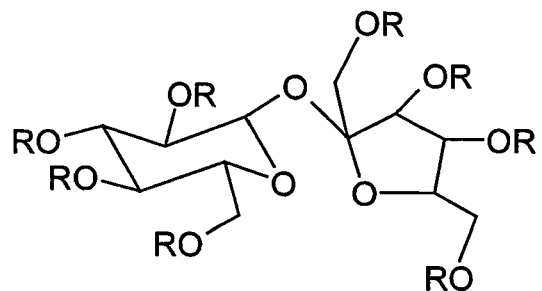
FIG. 1
FIG. 2
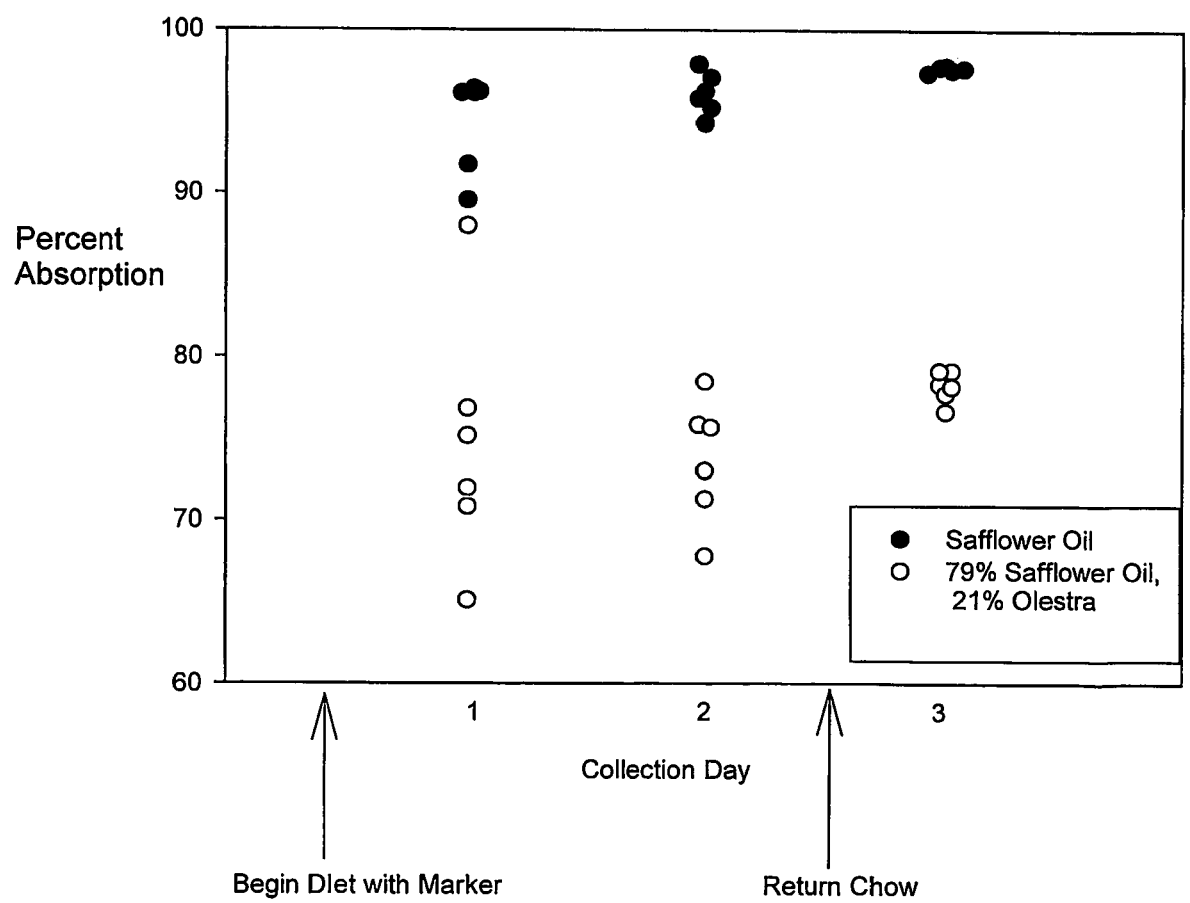

USE OF NON-ABSORBABLE FAT IN DETERMINING DIETARY FAT ABSORPTION

CROSS REFERENCE TO RELATED APPLICATIONS

This is the National Stage of International Application PCT/US2004/25350, with an international filing date of Aug. 5, 2004, which claimed the benefit of U.S. Provisional Application No. 60/481,187, filed Aug. 6, 2003.

TECHNICAL FIELD

The present invention relates to the field of fecal analysis to determine fat absorption by the digestive tract. The invention also relates to the diagnostic testing for diseases in which malabsorption of fats by the digestive tract is symptomatic or causative of those diseases.

BACKGROUND OF THE INVENTION

Chronic undernutrition resulting in significant weight retardation and linear growth failure has long been recognized as a general problem among cystic fibrosis patient populations, as well as those resulting from other diseases or syndromes of malabsorption of fat from the small intestine. It is well accepted in medical science that there is a significant correlation between the degree of malnutrition and the severity of such diseases. A variety of complex factors, both related and unrelated, can give rise to the energy imbalance underlying undernutrition or malnutrition that manifests in malabsorptive conditions. Nonetheless, fecal nutrient losses, including those of fat, from maldigestion or malabsorptive diseases are known to contribute to energy imbalance, and therefore point to the need for a convenient and accurate measure of fat absorption to improve diagnosis, management, and treatment of these conditions. While the normal value for total fat absorption in humans is >90% absorbed (<10% remaining in feces), it may be as low as 60% (40% remaining in feces) in association with conditions of atrophy of intestinal mucosa such as celiac disease, idiopathic steatorrhea, obstructive jaundice, chronic pancreatitis, cystic fibrosis, gastrectomy; intestinal resection or anomalies, blockage of intestinal lymphatics, iatrogenic steatorrhea caused by irradiation or antibiotics, pneumatosis intestinalis, or failure of blood supply such as mesenteric endarteritis.

Fat-balance methodology, which is based on the measurement of consumed and excreted fat, is a standard means for the assessment of the absorption of dietary fat. Fat-balance methodology can be used for indirect measurement of fat absorption because fat that is not absorbed in the small intestine is minimally altered during transit through the large intestine. Although hydrolysis of dietary triacylglycerol fats can be catalyzed by anaerobic bacterial lipases in the large intestine, long-chain fatty acids released from triacylglycerol fats are not utilized for energy in the colon and are excreted intact or with structural alterations limited to partial hydrogenation or migration of double bonds (Howard, F A et al. (1999). *Lett Appl Microbiol* 29:193-196). These alterations do not measurably affect the mass of unabsorbed fat that appears in feces. Therefore fecal fat reflects the type and amount of fat that exits the small intestine.

Although the basic concept of "fat intake minus fat output" is easily understood, the execution of the fat-balance method is difficult in practice. First of all, an accurate and complete measurement of diet composition and consumption is necessary for the calculation of fat absorption. Studies with rodents can be problematic if diet is spilled or scattered, thus making it difficult to determine the amount of diet that was consumed. Equally important is the complete collection of fecal matter at a time and of a duration corresponding to the test meals. This collection can require special metabolic cages for animal studies. Methods to help match fecal matter with corresponding test meals have included radio-opaque pellets in the diet with subsequent counting of the pellets in rodent feces.

Accurate and complete collection of human fecal matter is more problematic, and can involve a stay of 4-7 days in a metabolic ward. Current methodology is based on the assumption that all unabsorbed fat ingested from a test meal has been recovered in the collection of fecal material. Typically, all feces excreted during a 72-hour period following ingestion of a test meal are collected. Such a collection can be difficult to execute accurately, and can be an onerous task, as well as difficult to verify as complete. The difficult nature of the complete collection of fecal matter for clinical analysis can be more fully understood by the following description of the methodology taken from *Bray's Clinical Laboratory Methods* (CV Mosby Co., Library of Congress Catalog Card Number 68-55316, pg. 455), which represents the state of the art in collection of samples for fecal fat analysis: "Collection of the specimen presents some problems. The determination of fat on a random specimen is of little value. It is generally agreed that, if possible, all the stool excreted over a 3-5 day period should be collected for analysis. Also it is preferable that the patient be on a fairly constant diet, one in which the fat content is at least approximately known, for 2 or 3 days prior to and throughout the collection period. The samples should be preserved in the refrigerator until analyzed. If more than an occasional determination is made (i.e., multiple subjects are to be tested), it is helpful to collect the specimens in new pre-weighed 1-gallon metal paint cans. These have tight-fitting covers, and after the entire specimen has been collected it can be well mixed in the original can by adding some water if necessary and shaking on a paint-shaking machine. This usually gives a homogeneous sample. Subtract the weight of the can from the weight of the can plus contents to obtain the weight of the specimen. The addition of water makes no difference since one is determining the fat in an aliquot from an entire 3-day specimen. If the feces are collected in other containers, the entire specimen must be well mixed. This is best accomplished with a Waring blender or similar machine and with the addition of a small amount of water. The weight of the total homogenized specimen must then be obtained."

Because of the problems associated with complete collection of fecal specimens, other techniques have been used to estimate fat absorption (Hill, P G, (2001). *Ann. Clin. Biochem.* 38:164-167). For example, the measurement of the appearance of $^{14}CO_2$ in breath after consumption of $^{14}C$-triolein has been carried out. This approach gives a relative measure of absorption based on comparison with $^{14}CO_2$ in the breath of subjects for which fractional fat absorption is known. In a modification of this method to avoid exposure to radioactivity, dietary triacylglycerols containing $^{13}C$ have also been fed followed by subsequent measurement of expired $^{13}CO_2$ by mass spectroscopic analysis. Non-absorbable flow markers have also been used in the measurement of dietary lipid absorption. Cholesterol absorption has been measured by radioisotope techniques using dietary plant sterols as non-absorbable fat markers (see e.g., Jandacek, R J et al. (1990). *Metabolism,* 39:848-852). Dietary triacylglycerol absorption has been measured in rats by simultaneous feeding of $^{133}I$-triolein and the non-absorbable fat marker, $^{75}Se$-glyceryl triether (Hoving, J. et al. (1977). *Gastroenterology* 72:406-412). However, these markers obviously require ingestion of radioactive material, a procedure that has inherent limitations, and can have serious drawbacks for human subjects.

Non-radioactive safe markers that are measured by standard techniques have not been validated for use in measuring fat absorption. Currently, there are neither any known markers that are both safe and readily available for use in humans, nor methods for the use of use such a marker. Therefore, a need exists for an appropriate marker for dietary fat that: (1) is not absorbed; (2) has the physical properties of dietary triacylglycerol fats; (3) can be measured by standard gas chromatographic techniques; (4) is approved for use in humans, and (5) does not alter dietary fat absorption. Such a marker would also need to be readily available in sufficient, cost-effective quantities. Additionally, a method for measurement that did not require extensive collection and homogenization of fecal material would provide a significant advantage to both the subject and the administrator of the method. Therefore, a method that would allow measurements to be taken from relatively small samples taken at appropriate times would relieve all parties involved of the burden of extensive collection and storage of fecal materials.

BRIEF DESCRIPTION OF THE INVENTION

The present invention includes a use of sucrose polyester with behenate fatty acid chains as a non-absorbable fat marker to determine total dietary fat absorption by the digestive tract of a subject, and to diagnose impairment of dietary fat digestion and/or malabsorption of dietary fat.

The invention relates to a composition used as a test meal for use in measuring total dietary fat absorption by the digestive tract of a subject, comprising a predetermined amount of dietary fat and a predetermined amount of a non-absorbable fat marker. The fat marker can be sucrose polyester in the form of sucrose behenate, and is 0.1-10% by weight of the total of dietary fat and non-absorbable fat marker in the test meal. The test meal can further comprise an amount of protein and an amount of carbohydrate, and can be in the form of a liquid. The test meal can contain a colorant in a quantity sufficient to change the color of the fecal matter produced from the test meal.

The method for measuring total dietary fat absorption by the digestive tract of a subject comprises the steps of providing a test meal for consumption comprising an amount of dietary fat and an amount of a non-absorbable fat marker, administering ingestion of the test meal by the subject, collecting a sample of fecal matter at an interval following ingestion of the test meal, measuring the amount of the dietary fat and the amount of non-absorbable fat marker recovered in the fecal sample, and calculating the amount of dietary fat recovered from the test meal to determine the amount of dietary fat that was absorbed by the digestive tract of the subject. The composition of the test meal can further comprise an amount of protein and an amount of carbohydrate, and can be a liquid. The preferred non-absorbable fat marker is an amount of sucrose behenate, and is 0.1-10% by weight of the total of dietary fat and sucrose behenate in the test meal. The test meal can further comprise a colorant in a quantity sufficient to change the color of the fecal matter produced from the test meal. The methods of the invention can be used to diagnose malabsorption of dietary fat by the digestive tract of a subject, or impairment of dietary fat digestion.

BRIEF DESCRIPTION OF THE DRAWINGS

FIG. 1 shows the structural formula for sucrose polyester.

FIG. 2 shows fat absorption data in mice fed either a Safflower Oil Diet (closed symbols) or Safflower Oil and Olestra Diet (open symbols) using the method of the invention described in Example 1.

DETAILED DESCRIPTION OF THE INVENTION

1. Definitions

Figure 3:
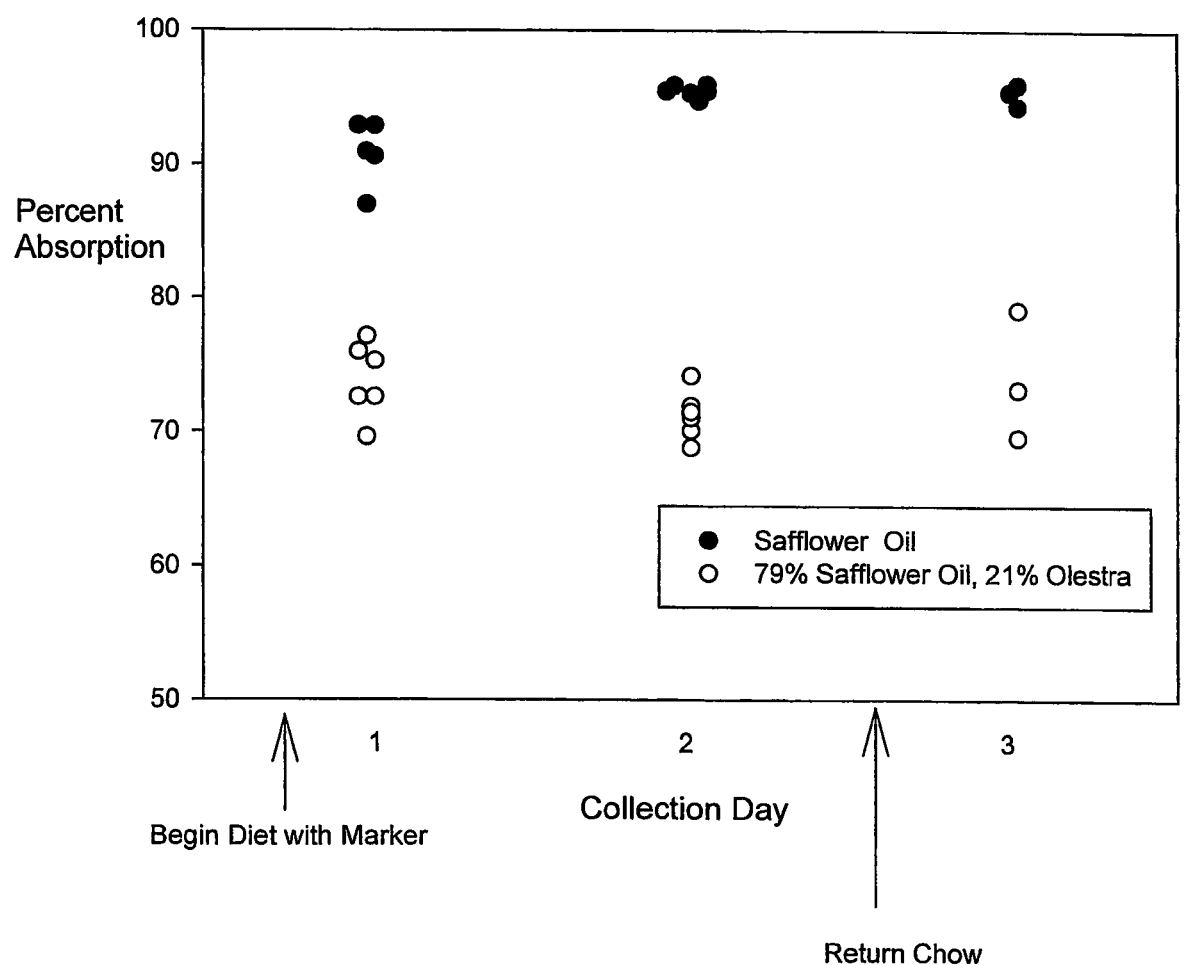
FIG. 3 shows total fat absorption in rats fed either a Safflower Oil Diet (closed symbols) or Safflower Oil and Olestra Diet (open symbols) using the method of the invention described in Example 2.

As used herein, the term sucrose polyester refers to a molecule having the general structure shown in FIG. 1, where R represents long-chain acyl chains. Long-chain fatty acids can include, but are not limited to palmitate, oleate, stearate, linoleate, and behenate chains.

As used herein, the terms "long-chain acyl chains", "fatty acids", and "fatty acid chains" are used interchangeably to refer to hydrocarbon chains that can be incorporated into larger hydrophobic molecules known broadly as fats or lipids.

As used herein, the terms "behenate" and "behenic acid" are used interchangeably to refer to fatty acid chains of 22 carbons with no double bonds.

As used herein, the terms "sucrose behenate" and "sucrose polybehenate" are used interchangeably to refer to a molecule having the structure of that shown in FIG. 1, where R represents long-chain acyl chains, principally behenate. At least 6 of the hydroxyl groups of sucrose are linked through ester bonds to fatty acids, which in part or completely comprise behenic acid.

As used herein, the term "non-absorbable fat marker" refers to a molecule or compound that passes through the mammalian gut at the same rate as the dietary fats with which it Is ingested, and is not taken up from the gut lumen into enterocytes, blood, lymph, or other organ system or biological compartment.

As used herein, the terms "feces", "fecal matter", "fecal material" are used interchangeably. The term "fecal pellet" is used to refer to feces excreted by rodents. The term "stool" is a clinical term that refers to feces excreted by humans.

The term "poorly absorbed colorant" or "colorant" refers to a molecule or compound that passes through the mammalian gut at a similar rate as the foods or meal with which it Is ingested, and is not taken up from the gut lumen in significant quantities, such that it imparts a color to the fecal material that is easily detected by the human eye.

As used herein, the term "test meal" (TM) refers to a food composition having a prescribed amount of calories comprising dietary fats, proteins, and carbohydrates, and is of sufficient calories as to provide a substitute for one meal. Such a test meal can comprise solids, liquids, or a combination of solid and liquid foods.

As used herein, the term "meal replacement" refers to a nutritionally complete substitute for a meal, such as Slimfast™, Jevity™, Ensure™, or similar liquid meal replacement drink.

As used herein, the term "test diet" refers to a series of test meals or a feeding regimen provided to rodents for a prescribed period of time.

As used herein, the term "fat absorption" refers to the transfer of dietary fats by the digestive tract into the blood, lymph, enterocyte, or other cells, bodily compartment or organ system.

As used herein, the term "ingestion" refers to the introduction of nutrients into the digestive tract. It is used interchangeably with "consumption", but also encompasses nutrients instilled directly into the esophagus, stomach, or intestines through tubing or ostomy orifices.

The present invention relates to the use of a marker for the intestinal flow of fat and its recovery in feces. The marker is a non-absorbable fat marker. Fecal matter produced from the test meal is collected at appropriate interval(s) following consumption of the test meal, and the amounts of non-absorbable fat marker and dietary fat are measured. The percent of dietary fat absorbed from the test meal is calculated using the following formula I:

$$\text{Fraction of absorbed fat} = \frac{\frac{F_d}{M_d} - \frac{F_f}{M_f}}{\frac{F_d}{M_d}} \quad (I)$$

where $F_d$=sum of the masses of all dietary fatty acids (or that of an individual fatty acid) other than non-absorbable fat marker in the test meal, $M_d$=mass of non-absorbable fat marker in the test meal, $F_f$=sum of the mass of all fatty acids (or that of an individual fatty acid) other than non-absorbable fat marker in the fecal sample, and $M_f$=mass of non-absorbable fat marker in the fecal sample.

Typically the marker is a sucrose polyester compound synthesized from sucrose and fatty acids. As used herein, both sucrose polyester and olestra refer to structures comprising hexa, hepta, and octa esters of long-chain fatty acids and sucrose. A preferred marker is made from sucrose and behenic acid, and is known as sucrose polybehenate or sucrose behenate. Typical characteristics for an appropriate non-absorbable fat marker for dietary fat are that: (1) it is not absorbed; (2) it has the physical properties of dietary triacylglycerol fat so that it passes through the gut at the same rate; (3) it can be readily measured using standard techniques such as gas chromatographic techniques; and (4) it does not alter dietary fat absorption. In addition, the methods require neither radioisotopes nor mass spectrometry. The use of sucrose behenate presently is of particular advantage. Another advantage of sucrose behenate is that it is easy to formulate meals or diets with no behenate compounds other than sucrose behenate, thereby facilitating analyses. Sucrose behenate is currently approved by the USDA as a safe ingredient for use in food preparation, and is both economical and readily available for use. Because of its use in food products, sucrose behenate is applicable to the measurement of fat absorption in humans as well as in experimental animals. Yet another advantage of the invention is that use of sucrose behenate enables an accurate estimate of fat absorption to be made from a very small sample of fecal material produced from a test meal that contains the marker.

The invention also relates to a food composition containing a non-absorbable fat marker. This food composition, called the "test meal" or "test diet", contains known amounts of dietary fats, proteins, and carbohydrates, with appropriate amount of each component as set forth by the USDA according to age, gender, or species. This test meal can include solid and/or liquid components. The preferred embodiment for human subjects is a liquid, similar to a meal replacement drink such as Slimfast™, Jevity™, or Ensure™, comprising the amounts of dietary fats, proteins, and carbohydrates according to USDA guidlines. Typically, these amounts would fall within 5-60% for dietary fats, 1-25% for proteins, and 5-60% for carbohydrates, by weight. The non-absorbable fat marker can be included as an ingredient within the test meal, or can be contained in a capsule that is ingested with a test meal.

The present invention is also a method for measuring total fat absorption by the digestive tract of a subject, wherein a test meal or series of meals comprising amounts of a dietary fat and a non-absorbable fat marker are provided for ingestion. The non-absorbable fat marker is typically a synthetic fat molecule known as -sucrose polyester. Sucrose polyester is available from The Procter & Gamble Company under the names olestra or Olean™.

The structural formula for sucrose polyester is a sucrose ring such as that of sucrose polyester, where R represents long-chain acyl chains. Sucrose behenate is a sucrose polyester molecule that primarily comprises behenate long-chain acyl chains. Sucrose behenate is currently part of the olestra in the non-digestible oil Olean® (Procter & Gamble Co.). Olean® is a blend of long-chain fatty acid esters of sucrose that is used in the commercial preparation of snack foods. Approximately 77% of the long-chain acyl chains in the sucrose behenate used in Olean are behenate. Sucrose behenate is particularly useful in the present invention due to its physical properties that are similar to dietary fats. The physical properties of sucrose behenate and olestra are virtually identical to those of triacylglycerols with the same fatty acid composition, so that it passes through the digestive tract at the same rate as triacyglycerols (Jandacek, R J et al. (1978) *Chem. and Physics of Lipids,* 22:163-176), but it is not hydroylyzed by pancreatic lipase and therefore not absorbed from the intestine (Miller, K W et al. (1995). *Fundam Appl Toxicol* 24:229-37.). Another important characteristic of sucrose esterified with long-chain fatty acids, such as sucrose behenate and olestra, is that it does not interfere with the absorption of dietary triacylglycerols (Fallat, R W et al. (1976) *Am J Clin Nutr.* 29: 1204-15) and Daher, G C et al. (1997) *J Nutr* Aug; 127(8 Suppl):1694S-1698S). When used as a dietary fat substitute in a food composition, sucrose behenate content of about 20% or less (by weight of total dietary fat) will typically maintain the original appearance or taste of most foods. However, when added in excess of about 20% of total dietary fat, sucrose behenate will impart a waxy consistency to the food composition.

Behenic acid is found only in trace quantities in dietary fats and oils with the exception of peanut oil, in which it accounts for approximately 3% of the fatty acids (Ensminger, A H et al (eds). The Concise Encyclopedia of Foods and Nutrition, CRC Press, Boca Raton, 1995, p. 802). It is possible to provide a diet for an adequate number of days prior to testing that contains no behenic acids. Therefore, markers containing behenic acid moieties can be used to estimate of the absorption of dietary fats when peanut oil has been eliminated, at least temporarily, from the diet of the subject to be tested, and is not contained in the test diet or meal. This is because, in contrast to the synthetic sucrose behenate molecules, naturally occurring dietary fats comprising behenate will be hydrolyzed in the digestive tract and absorbed to varying degrees.

It can be appreciated that various fecal samples collected following ingestion of the test meal will contain varying amounts of the behenic acid and unabsorbed dietary fat. However, the methods of the present invention can be used to determine the ratio of behenic acid and unabsorbed dietary fat in any sample that is produced from the test meal, and will be sufficient to determine the total amount of unabsorbed dietary fat from the entire meal. This is because the calculation is dependent upon a ratio of the sucrose behenate to the dietary fat in the feces, making complete collection of all fecal matter produced from the test meal unnecessary. Because the behenic acid will travel through the digestive tract at the same rate as the dietary fats, the ratio will remain constant. Therefore, a relatively small sample is sufficient to provide the ratio that will allow accurate estimation of the total amount of fat absorbed from the test meal.

The test meal can comprise known amounts of any suitable dietary fat, protein, and carbohydrate, preferably meeting the Recommended Daily Allowances (RDA) for these components as set forth by the USDA according to age, gender, and species. Examples of such a test meal can include solid and/or liquid components, but the preferred embodiment is a liquid meal-replacement drink to which the marker is added. An example of a meal replacement drink includes Slimfast™, Boost™, or Jevity™, as long as the amounts of dietary fats, proteins, and carbohydrates are known. In some instances, the test administrator can determine that a series of test meals should be ingested. This would especially be preferred when the test subjects are animals. In the case of animals, the meals can more conveniently be considered as a test diet which is provided to the animals over a defined period of time, for example 1-2 days or nights, especially when testing nocturnal rodents.

The test meal or diet can be most conveniently administered when the subject is able to freely consume the meal or diet. However, circumstances can dictate that the test meal or diet be administered via tube feeding directly into the digestive tract via any suitable natural or surgically designed orifice. Such administration can occur by a variety of means well known to those skilled in the art, and is meant to be encompassed by definition in the term "ingest" or "ingestion". Administering ingestion can include providing written or oral instructions for ingestion in the presence of the administrator, or remotely, such as at home).

A sample of fecal matter produced from a test meal is collected at an interval following ingestion of the test meal. In general, the fecal matter produced at an interval of one day following ingestion of the test meal will be the product of the test meal. In cases of uncertainty, small samples can be collected daily for several days following ingestion of the test meal, until the samples are determined to contain the nonabsorbable fat marker. This is a particular convenience of the methods of the present invention, since very small individual samples (10-20 milligrams) are sufficient for analysis and calculation. However, samples of approximately 1-2 grams collected from human feces will increase the accuracy of the measurement, and is preferred. To aid in the visual recognition of the desired fecal matter, non-toxic poorly absorbed dyes or colorants can be ingested in or with the test meal to provide a color cue to identify the product of the test meal. Examples of such colorants and the colors they impart include, but are not limited to, beta-carotene (orange), bromophenol blue (green or blue, depending on pH), cresol green (green), and carmine red (red), individually or in combinations. Other non-toxic, poorly absorbed dyes or colorants may also be used individually or in combinations with essentially the same purpose and result.

The dietary fat and sucrose polybehenate content contained in the fecal sample is measured by any conventional means well-known to those of ordinary skill in the art, and the amount absorbed by the digestive tract is calculated indirectly. Examples of such means include, but are not limited to gas chromatography, HPLC, and mass spectrometry. The use of HPLC methodology also allows one to measure total sucrose polyester in feces as an alternate method to the use of sucrose behenate. However, this method is analytically more difficult than using sucrose behenate, which is converted to methyl esters and measured by gas chromatography methodology.

The disclosed embodiments demonstrate that sucrose behenate can function as a marker for the measurement of the absorption of dietary fat. The use of sucrose behenate provides a facile, accurate, isotope-free, non-invasive method for the assay. The safety and availability of the marker allow its application in fat absorption measurements in humans. Its use would greatly reduce the difficulties inherent in the collection of multi-day fecal collections from humans by requiring only a small sample of the total fecal material that would ordinarily need to be collected.

EXAMPLES OF THE INVENTION

The following specific examples are provided to describe embodiments of the invention, which show the use of sucrose polyester as a means to measure fat absorption from the gut, and/or to diagnose or assess maladies involving impairment of fat digestion and/or absorption. In examples of the invention for diagnosis of conditions of malabsorption, (1) olestra or (2) calcium soaps are added to dietary fats or oils in-test diets to provide fecal fat in the two principal forms in which it occurs in conditions of malabsorption. These two forms are (1) unhydrolyzed triacylglycerol and (2) salts of fatty acids (soaps) (Khouri, M R et al. (1989) *Gastroenterology* 96:848-852). Because of the physical similarity of olestra and triacylglycerols (Jandacek, 1978), olestra is used in a blend of dietary fats in Examples 1 and 2 as a model for the assessment of unhydrolyzed fecal triacylglycerols), since olestra is not digested or absorbed in the mammalian. Thus, feeding rodents a diet of olestra and triacylglycerols, such as safflower oil, mimics an "impaired" malabsorptive gut for validation of the methods of the present invention. Bacterial lipases can hydrolyze a portion of undigested triacylglycerol that enters the colon to form fatty acids and their soaps. Example 3 includes direct measurement of the absorption of stearic and palmitic acids in the form of calcium soaps as a model of malabsorption of fatty acids in the form of salts.

Methods Used In Practicing The Invention

The following summarizes methods used in examples of the invention, and will be referred to in each of the examples.

1. Methods for Preparation of Test Diets and Test Meals

"Safflower Oil Diet" is a food for rodents prepared with a fat content of 95% safflower oil and 5% sucrose behenate. "Safflower Oil and Olestra Diet" refers to food for rodents prepared with a fat content of about 79% safflower oil and about 21% olestra. The 21% olestra portion of the Safflower Oil Diet comprised about 95% olestra and about 5% sucrose behenate. The composition of the principal fatty acids of olestra used in the following examples of the invention is about 22.3% palmitic, 3.7% stearic, 27.5% oleic, 32.9% linoleic, and 5.1% behenic by weight. The fatty acid composition of the sucrose behenate used in the following examples of the invention is about 2.0% palmitic, 3.1% stearic, 7.1% oleic, 2.9% linoleic, 5.1% arachidic, and 77.0% behenic by weight. Thus sucrose behenate was approximately 1% of the total Safflower Oil and Olestra Diet. These two diets further have the following composition by weight: about 16% fat, 45% non-fat dry milk, and 39% sucrose, providing 30:15:55 fat:protein:carbohydrate energy %. Non-fat dry milk comprised 60% carbohydrate and 40% protein by weight. The fat composition (% by weight) is given for each diet as listed below. Safflower oil is mixed with sucrose behenate or olestra and sucrose behenate at 80° C. until melted to a clear liquid. Aliquots of approximately 10 microliters of each fat blend are set aside and later analyzed for fatty acid analysis. The fat blends are added to non-fat dry milk and sucrose and mixed with an electric mixer for 5 minutes. The prepared diets are placed in a capped glass bottle and stored at 4° C. until used.

"Safflower Oil and Calcium Soaps Diet" is a food prepared for rodents with a fat content of about 95% safflower oil and about 5% calcium soaps of stearic and palmitic acid. An amount of sucrose behenate is added to the Safflower Oil and Calcium Soaps diet, such that, based on the total of all fat components in the diet, sucrose behenate is 5% by weight, along with 5% calcium stearate-palmitate, and 90% safflower oil. The calcium soap is derived from a mixture of stearic (63.8%) and palmitic acid salts (28.8) obtained from Witco (Memphis, Tenn.). To make the Safflower Oil and Calcium Soaps Diet, safflower oil is mixed with sucrose behenate at 80° C. until melted to a clear liquid, and the calcium soap mixture is dispersed in this oil. The fat blend is added to the non-fat dry milk and sucrose and mixed with an electric mixer for 5 minutes. Three aliquots of the fat blend are set aside and later analyzed for fatty acid analysis. The prepared diet is placed in a capped glass bottle and stored at 4° C. until used.

A Test Meal (TM) provided for human subjects in the following examples refers to a liquid meal replacement drink with 0.5-3% by weight sucrose behenate added. The meal replacement drink contains an amount of fat, protein, carbohydrate and water in nutritionally appropriate proportions suitable for human subjects. The proportions of fat, protein, and carbohydrate conform to the guidelines set forth by the USDA for the RDA according to age and gender. Test Meal-C (TM-C) refers to the same liquid meal replacement drink with 0.5-3% by weight sucrose behenate added, and ingested along with a gelatin capsule containing up to 1 gram of bromophenol blue.

2. Rodent Feeding and Fecal Collection Regimen

The feeding and fecal collection regimen for rodents includes two days of test diet and three days of fecal collection. Prior to the study, the animals eat commercial chow ad libitum. Test diets, also fed ad libitum, replace chow on days 0 and 1, and chow is returned to the animals on day 2. Fecal collections are made on days 1, 2, and 3. The feeding and feces collection regimen is illustrated in the following table A:

TABLE A

| Day 0 | Day 1 | Day 2 | Day 3 |
|---|---|---|---|
| Introduce Test Diet | Collect Feces Continue Test Diet | Collect Feces Return Chow Diet | Collect Feces Continue Chow Diet |

3. Fat Extraction Protocol

This protocol is used for preparation of fecal samples for fat and sucrose behenate analysis. In general sample sizes of 10-20 milligrams provide a 5 to 10-fold excess of behenate in terms of the sensitivity of the gas chromatograph. The weighed fecal sample is ground into small particles with a spatula and placed in a 20 mL vial for saponification, methylation, and extraction. The method for saponification and methylation of fatty acids for gas chromatographic analysis can be that reported by Mecalfe (Metcalfe, L D et al. (1966). Anal. Chem. 38: 514-515). Four mL of 0.5N methanolic sodium hydroxide are added to the vial, which is then heated in a water bath at ~80° C. for 5 mins. After a brief cooling period, 3 mL of $BF_3$ in methanol (14% borontrifluoride and 86% methanol) are added to methylate the sample. After another five minutes of heating in the waterbath, the sample vial is allowed to cool to allow handling. Two mL of a saturated solution of sodium chloride and 10 mL of hexane are added to the vial. The samples are then mixed with a vortex mixer for one minute. Centrifugation can be used (2500 rpm at 1 min) to expedite the process of separation into two layers. The hexane fraction is transferred by pipette into a 20 mL vial that contains ~10 mg of sodium sulfate to dry the sample. The hexane solution is removed for gas chromatograph analysis. An injection volume of 1 μL of the 10 mL of hexane is analyzed.

4. Gas Chromatography Protocol

Samples are analyzed with a gas chromatograph (GC) such as a Shimadzu GC-17A equipped with autosampler and autoinjector. Analysis of fatty acid methyl esters is then based on areas calculated with Shimadzu Class VP 4.3 software. An example of an appropriate column is one that can be obtained from J&W Scientific, DB-23 (123-2332): 30 m (length), I.D. (mm) 0.32 widebore, film thickness of 0.25 μM, although any suitable column can be substituted. Fatty acid identification is made by the use of comparison of retention times with those of authenticated standards. The conditions for the GC analysis in the present example are: Column temperature ramping by holding at 120° C. for one minute followed by an increase of 5° C./min from 120-240° C. The temperature of the injector and flame ionization detector is 250° C. A split (8:1) injection mode is used. The carrier gas is helium with a column flow rate of 2.5 mL/min. Under these conditions, the retention time of methyl behenate is 18.7 min.

5. Fat/Marker Recovery Calculation

The absorption of fatty acids is calculated with formula II:

$$\text{Fraction of absorbed fat} = \frac{\frac{F_d}{B_d} - \frac{F_f}{B_f}}{\frac{F_d}{B_d}}$$

where $F_d$=sum of the masses of all dietary fatty acids (or that of an individual fatty acid) other than behenic acid,
$B_d$=mass of dietary behenic acid,
$F_f$=sum of the mass of all fecal fatty acids (or that of an individual fatty acid) other than behenic acid, and
$B_f$=mass of fecal behenic acid.

This method can be applied both to total and to individual fatty acids. (Identification of individual fatty acids can be diagnostic for some digestive deficiencies.) All masses are relative, and are expressed as areas of gas chromatograph responses of the methyl esters.

Example 1

Fat absorption from the Safflower Oil Diet and the Safflower Oil and Olestra Diet is compared in C57B1/6 male mice at least 5 weeks of age. Three mice housed in a first cage receive the Safflower Oil Diet, and three mice housed in a second cage receive the Safflower Oil and Olestra Diet. Essentially all of the feces from the second day's collection (after two days in which the animals received the test diet) are light in color. This appearance contrasts with the collections after the first day of feeding, in which approximately equal amounts of dark and light fecal pellets appeared. On the third collection day, most of the feces are dark in appearance. Intact single fecal pellets from mice (6-29 mg) are analyzed using the Fat Extraction and Gas Chromatography Protocols. Corresponding with transit of the diets through the gut, the darker feces contain only traces of behenic acid. Therefore, only the values obtained from light-colored fecal pellets are considered for calculation of fat recovery. The Fat/Marker Recovery Calculation is used to indirectly calculate the amount of fat absorbed from the test diets. The individual sample data for each day are shown in FIG. 2. The behenic acid in feces collected from the Safflower Oil Diet animals is in the range of 33.5-66.4% of the total fatty acids. The absorption of fat by the mice fed safflower oil is essentially complete. The absorption is calculated to be 95.9±0.5% (mean±SEM) of that which was fed, based on the 17 fecal samples that were collected over the 3 days. The absorption of 3 individual fatty acids from safflower oil is nearly complete for linoleic, oleic, and palmitic acids. Stearic acid absorption is less complete, with absorption of 77.3±2.1%, based on the 17 samples collected over 3 days.

By comparison, the absorption of total fat by the mice fed the Safflower Oil and Olestra Diet is markedly less than that absorbed by the group fed the Safflower Oil Diet. In this same time period, behenic acid accounts for 12.5-19.3% of the fatty acids in the feces from the animals fed the Safflower Oil and Olestra Diet. The mean (±standard error) percent absorption of total dietary fat calculated for days 1, 2, and 3, was 74.6±0.3, 73.7±1.6, and 78.2±0.4 respectively. The small variability of results among individual fecal samples suggests that a single fecal pellet from a mouse on the second day is sufficient for analysis and the accurate measurement of absorption, although collection of several samples would be preferred.

The following table B compares the fatty acid composition of olestra and of the fecal samples from the mice ingesting the Safflower Oil and Olestra Diet in this example.

TABLE B

| Fatty Acid | In Olestra (%) | Percent in Feces (Mean ± SEM) |
|---|---|---|
| Palmitic | 20.0 | 18.3 ± 0.5 |
| Stearic | 4.0 | 5.28 ± 0.3 |
| Oleic | 24.9 | 24.7 ± 01.0 |
| Linoleic | 30.0 | 27.7 ± .6 |

The fatty acids comprising olestra are reflected in the fatty acids recovered from the feces of animals fed the Safflower Oil and Olestra Diet. The use of sucrose behenate as a marker in the calculation of the absorption/excretion of olestra yields values that are consistent with its non-absorbability. The results are also consistent with the finding of slightly lower absorption of stearic acids compared with palmitic, oleic, and linoleic fatty acids. The ratio of behenate to other fatty acids is essentially constant for all three days of fecal collection. These results are consistent with sucrose behenate moving through the gastrointestinal tract with the unhydrolyzed fat. This example demonstrates the utility of the invention for measuring total dietary fat absorption, and for diagnosis of malabsorptive conditions.

Example 2

Fat absorption is measured in two rats fed the Safflower Oil Diet, and two rats fed the Safflower Oil and Olestra Diet. The rats are housed in individual cages. As noted in Example 1, the feces following the second day of test diet are all light in appearance. The feces following the first day are essentially all dark in appearance, as are those from the third collection period, which follows the return to chow. Based on findings in Example 1, light colored fecal pellets were selected for analysis. Approximately 10 mg of randomly sampled portions of feces from rats were used for sample preparation and analysis, using the Fat Extraction and Gas Chromatography Protocols. The Fat/Marker Recovery Calculation is used to indirectly calculate the amount of fat absorbed from the test diets. The absorption is calculated to be 95.4±0.5% (mean±SEM) of that which was fed, based on the 14 fecal samples that are collected over the 3 days, shown in FIG. 3. Based on the values from the fecal collections of days 2 and 3, the absorption of linoleic acid from safflower oil is essentially complete. The absorption of oleic and palmitic acids is similar (90.9±0.5 and 90.1±0.3%, respectively), and that of stearic is less complete (75.9±0.3%). The absorption of dietary fat by the Safflower Oil and Olestra Diet-fed animals was calculated to be 71.2±0.7% based on the fecal collections for day 2 and 3. The small variability of results among individual fecal samples suggests that the samples of 10 mg of rat feces were adequate for analysis. This example demonstrates the utility of the invention for measuring total dietary fat absorption, and for diagnosis of malabsorptive conditions.

Example 3

Figure 4:
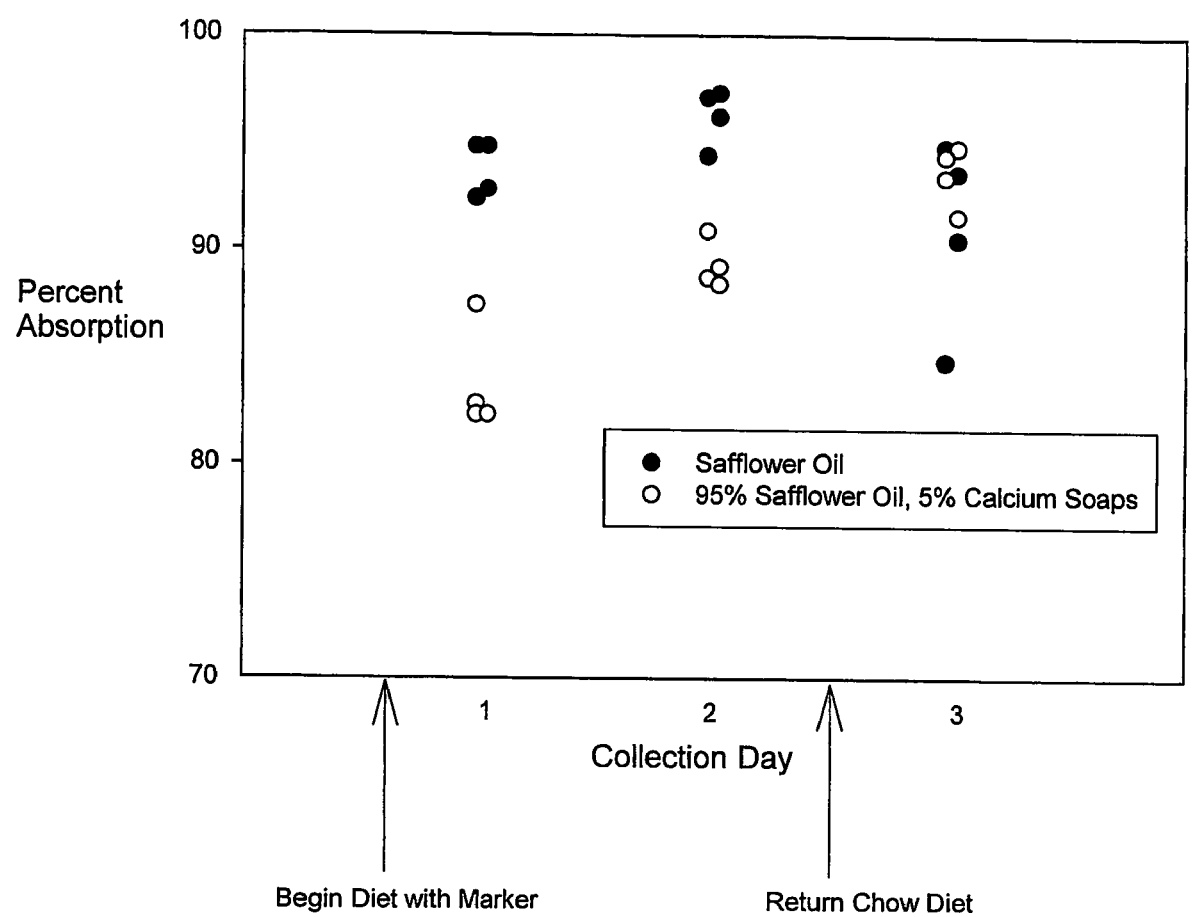
FIG. 4 shows total fat absorption in mice fed either a Safflower Oil Diet (closed symbols) or Safflower and Calcium Soaps Diet (open symbols) using the method of the invention described in Example 3.

Fat absorption is measured in three C57B1/6 female mice at 5 weeks of age that are provided with the Safflower Oil Diet, and three that are provided with the Safflower Oil and Calcium Soaps Diet. The appearance of the feces follows a pattern similar to that seen in Examples 1 and 2. Essentially all feces are dark in appearance in the first collection, all are light in the second collection, and all are mostly dark in the third collection. Four light colored samples are analyzed, using the Fat Extraction and Gas Chromatography Protocols. The Fat/Marker Recovery Calculation is used to indirectly calculate the amount of fat absorbed from the test meals. Results are shown in FIG. 4. The total fatty acid absorption for animals being fed the Safflower Oil Diet is similar to that of the examples described above—94-97% (96.3±0.7%, mean and standard error) based on the collection on Day 2, and the total fatty acid absorption by the group fed the Safflower Oil and Calcium Soaps Diet ranges from 88-91% (mean of 89.3±0.6%). Stearic acid absorption on Day 2 is 82.2±5.6% for the group fed the Safflower Oil Diet, and 13.1±5.6% for the group fed the Safflower and Calcium Soaps Diet. Palmitic acid absorption is 92.4±1.2% after the Safflower Oil Diet, and 66.4±2.1% after the Safflower Oil and Calcium Soaps Diet.

The small variability of results among individual fecal samples suggests that a single fecal pellet from a mouse on the second day is sufficient for analysis and the accurate measurement of absorption, although collection of several samples is preferred.

Based on the collection from Day 2, the absorption of fat by the Safflower Oil Diet group was 7% greater than that of the Safflower Oil and Calcium Soaps Diet group. This difference is consistent with the non-absorbability of the calcium salts of long-chain fatty acids. The calculations of stearic acid and palmitic acid excretion after ingestion of calcium soaps of these fatty acids are consistent with similar transit patterns for sucrose behenate and the fatty acid salts during the two days that followed administration of the diets. This example demonstrates the utility of the invention for measuring total dietary fat absorption, and for diagnosis of malabsorptive conditions.

Example 4

Six individually caged mice are fed powdered diet containing 20% fat used in Studies 1 and 2 to compare the sucrose behenate method with a total fat balance method well known to those skilled in the art. Measurement using the fat balance method is confounded by mice that refuse or spill a portion of the diet. The spillage of diet would be expected to result in diet intake estimates and calculated absorption (by fat balance) that are higher than the true values. The use of total collections also limits the measurement of individual fecal pellets in some animals. However, absorption can still be measured from the fecal homogenate by the sucrose behenate method for all 6 animals, since measurement of total diet consumption is not required.

Figure 5:
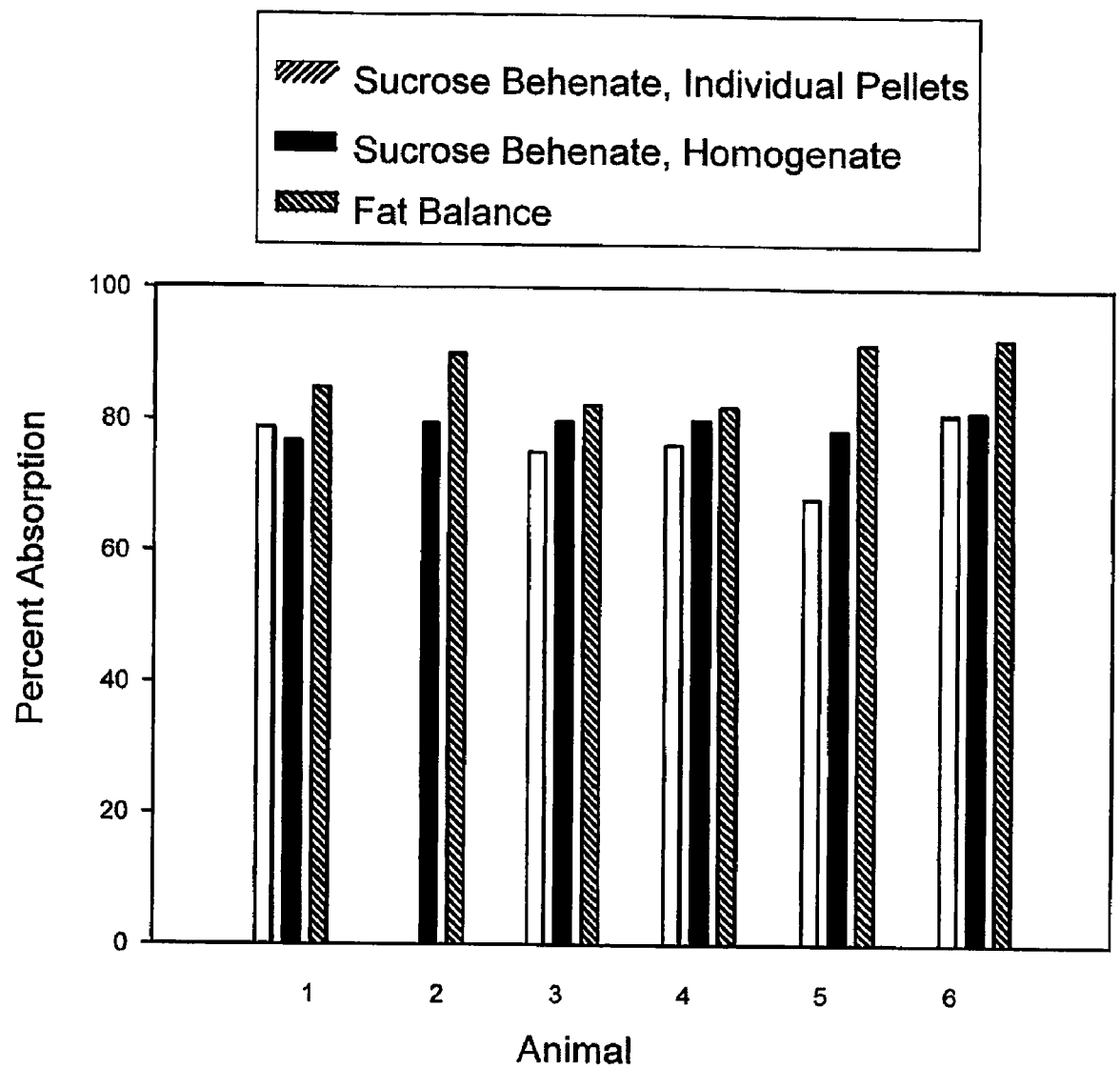
FIG. 5 shows fat absorption calculated by a sucrose behenate method applied to individual fecal pellets and to aliquots of a fecal homogenate, and by a fat-balance method calculated from total diet intake and total fecal excretion, under conditions where determination of total diet intake is difficult to determine for some animals.

Results of this study are shown in FIG. 5. The absorption calculated from the individual pellets by the sucrose behenate method (white bars) is 75.7±2.2% (n=5). Based on the sucrose behenate method applied to fecal homogenates (black bars), the absorption is 79.6±0.5% (n=6). Fat balance methodology (cross-hatched bars) gives a mean absorption of 87.1±1.9% (n=6), and this value differs from the absorption calculated by the sucrose behenate methods (P<0.05). This example demonstrates the utility of the invention despite difficulty that arises when total fat consumption cannot easily be determined.

Example 5

Six mice are fed a low-fat (5% by wt) semisolid diet. The diet fat includes 20% olestra and 80% safflower oil. The semisolid diet remains in the feed cup with minimal loss due to scattering. Fat balance is calculated based on the total diet consumption (day 2-3) and total fecal excretion (day 4). The sucrose behenate method is used with 3 fecal pellets per animal. In addition, the sucrose behenate method is applied to aliquots from the same fecal homogenate used in the total fat balance method.

Figure 6:
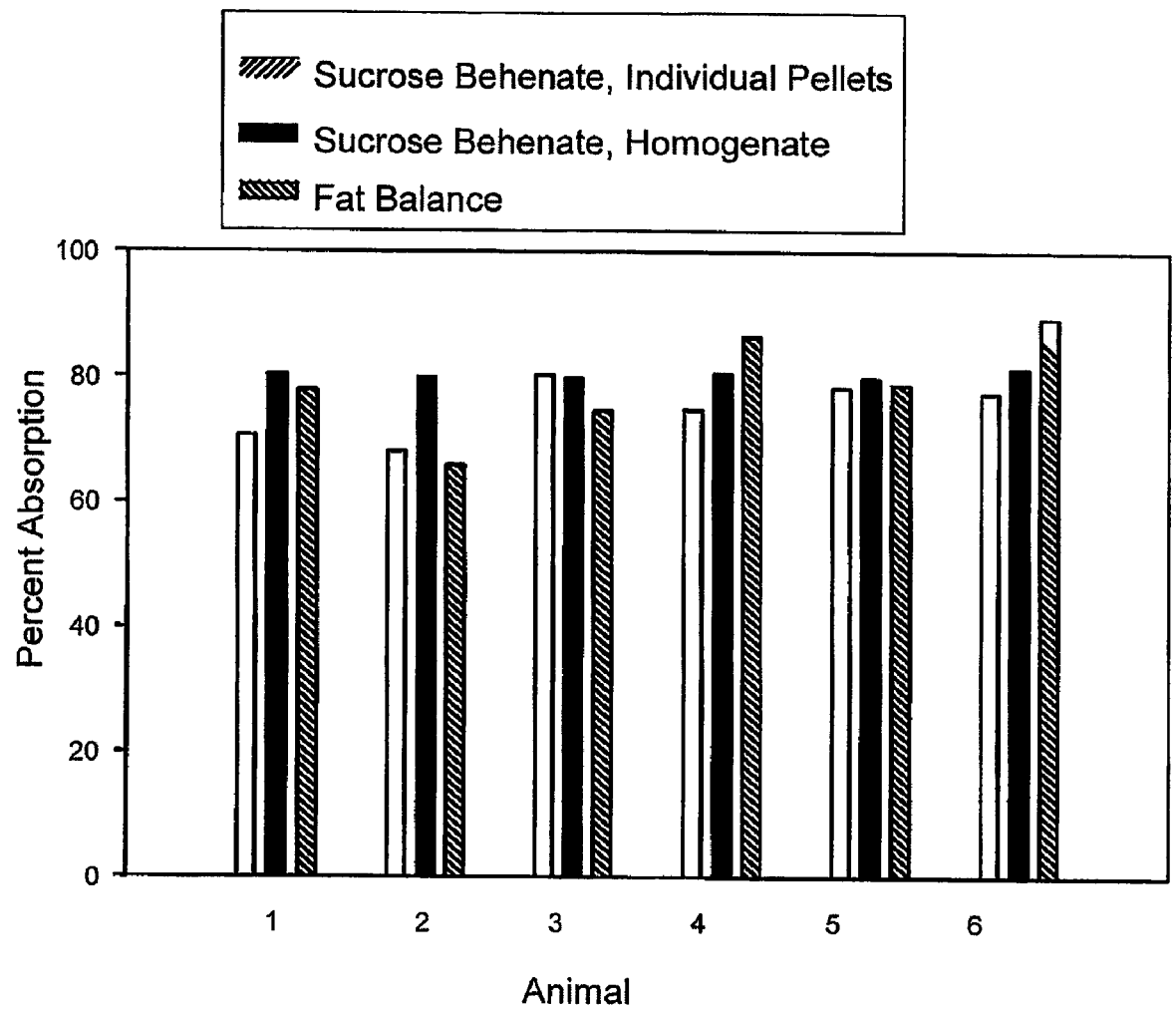
FIG. 6 shows fat absorption calculated by a sucrose behenate method applied to individual fecal pellets and to aliquots of a fecal homogenate, and by a fat-balance method calculated from total diet intake and total fecal excretion, following consumption of a low fat diet.

The results for the individual animals are presented in FIG. 6. The absorption calculated from the individual pellets by the sucrose behenate method (white bars) is 74.8±1.9% (n=6). Based on the sucrose behenate method applied to fecal homogenates (black bars), the absorption is 80.2±0.26% (n=6). Fat balance methodology (cross-hatched bars) gave a mean absorption of 78.7±3.4% (n=6). The values obtained by the three measurements did not differ by a statistically significant degree. This study demonstrates that the sucrose behenate method is accurate and effective when measuring fat absorption from a low-fat diet.

Example 6

A Test Meal (TM) is provided for consumption by a human subject. A Test Meal with carmine red colorant (TM-C) is provided for consumption by a second human subject. Following an overnight fast, each subject consumes the assigned test meal as a replacement for breakfast. The remaining meals of the day provide only very small quantities of fat. The subject collects a sample of each stool excreted during the two days following ingestion of the TM. The subject consuming the TM-C collects a sample of each stool with a red appearance excreted during the two days following ingestion of the TM-C. Samples of 10-20 mg of feces are stored in 20 mL vials at 4° C. Stool samples are prepared and analyzed using the Fat Extraction and Gas Chromatography Protocols. Sucrose behenate is found in two of the five samples collected by the subject consuming the TM; only those two samples are used to calculate total dietary fat absorption. Sucrose behenate is found in each of the two samples collected by the subject consuming the TM-C; both values are used to calculate total dietary fat absorption. The Fat/Marker Recovery Calculation is used to indirectly calculate the amount of fat absorbed from the test meals. Both subjects are found to have >92% total fat absorption, demonstrating normal fat digestion and absorption. This example demonstrates the utility of the invention as a method for determining total fat absorption, confirming the absence of disorders associated with malabsorption or digestion of fat. This example also demonstrates the added convenience of a colorant in reducing the number of samples that need to be collected, stored, and analyzed.

Example 7

A diet comprising solid and liquid foods is prescribed for three test meals, with total dietary fat content of the three meals calculated using tables such as those found in standard reference texts. Examples of such reference texts Contemporary Nutrition, Wardlaw, G. M. et al. Mosby, St. Louis, 1992; or The U.S. Department of Agriculture National Nutrient Database for Standard Reference, Release 15. Each of the meals contains the same amount of dietary fats. Following an overnight fast, each subject consumes the three test meals over the course of one day in place of normal diet. A capsule containing 0.5 grams of sucrose behenate is ingested with each of the three meals. Samples of 10-20 mg of any stools excreted during the following two days are collected are in 20 mL vials and stored at 4° C. All stool samples are prepared and analyzed using the Fat Extraction and Gas Chromatography Protocols. Those samples containing sucrose behenate are used in the Fat/Marker Recovery Calculation to indirectly calculate the amount of fat absorbed from the test meals. One of the subjects is found to have 94% total fat absorption, demonstrating normal fat digestion and absorption. The second subject was found to have 72% total fat absorption, confirming a diagnosis of malabsorption of fats due to lipase insufficiency. This example demonstrates the utility of the invention as a method for determining total fat absorption and for diagnosis of disorders associated with malabsorption or digestion of fat.

We claim:

1. A method for measuring total dietary fat absorption by the digestive tract of a subject, useful for diagnostic testing for diagnosing malabsorption of dietary fat by the digestive tract of the subject, and impairment of dietary fat digestion in the subject, comprising the steps of:
   a. providing a test meal for consumption, comprising a predetermined amount of dietary fat and a predetermined amount of a marker consisting of sucrose polyester comprising sucrose behenate, b. administering ingestion of the provided test meal by a subject under diagnosis for malabsorption of dietary fat by the digestive tract of the subject or an impairment of dietary fat digestion in the subject, c. analyzing for the amount of total fatty acid in the dietary fat and the amount of behenic acid in the sucrose polyester recovered in a sample portion of fecal matter collected from the stool of the subject at an interval following ingestion of the provided test meal wherein the sample portion does not result from the homogenization of an entire stool collected from the subject, and d. calculating the amount of dietary fat recovered from the provided test meal based on the analyzed amounts of total fatty acid and behenic acid, to determine the amount of dietary fat that was absorbed by the digestive tract of the subject.

2. The method according to claim 1, wherein the provided test meal further comprises about 1 to 25% protein, and about 5 to 60% carbohydrate, by weight.

3. The method according to claim 2 wherein the provided test meal comprises 0.1% to 10% sucrose behenate by weight of the dietary fat.

4. The method according to claim 2 wherein the amount of the collected fecal sample portion is from about 10 milligrams to about 2 grams 5. The method according to claim 4 wherein the amount of the collected fecal sample portion is from about 10 milligrams to about 20 milligrams 6. The method according to claim 5 wherein the provided test meal further comprises a colorant, in an amount sufficient to change the color of the fecal matter produced from the provided test meal, such that the sample portion collected from the subject is colored according to the colorant used.

7. The method according to claim 1 wherein the sucrose polyester in the provided test meal comprises sucrose behenate at up to 20%, by weight of the dietary fat.

8. The method according to claim 7 wherein the provided test meal comprises 0.1% to 10% sucrose behenate by weight of the dietary fat.

9. The method according to claim 8 wherein the provided test meal further comprises a colorant, in an amount sufficient to change the color of the fecal matter produced from the provided test meal, such that the sample portion collected from the subject is colored according to the colorant used.

10. The method according to claim 1 wherein the sample portion of the fecal matter is collected during the day following ingestion of said test meal, or during each of the two consecutive days following ingestion of the provided test meal.

11. The method according to claim 1 wherein the provided test meal further comprises a colorant, in an amount sufficient to change the color of the fecal matter produced from the provided test meal, such that the sample portion collected from the subject is colored according to the colorant used.

12. The method according to claim 11 wherein the colorant is selected from the group consisting of bromophenol blue, cresol green, beta-carotene, and carmine red, and mixtures thereof.

13. The method according to claim 1 wherein the sucrose polyester consists of sucrose behenate.

14. The method according to claim 1 wherein the test meal is in liquid form.

15. The method according to claim 1 wherein the test meal comprises 5 to 60% dietary fat, by weight.

16. The method according to claim 1 wherein the amount of the collected fecal sample portion is from about 10 milligrams to about 2 grams.

17. The method according to claim 16 wherein the amount of the collected fecal sample portion is from about 10 milligrams to about 20 milligrams.

18. The method of claim 1 wherein the step of analyzing comprises i) collecting a sample portion of fecal matter from the stool of the subject at an interval following ingestion of said test meal wherein the sample portion does not result from the homogenization of an entire stool collected from the subject, and ii) analyzing for the amount of total fatty acid in the dietary fat and the amount of behenic acid in the sucrose polyester recovered in the sample portion.

19. The method according to claim 1 wherein the provided test meal comprises 0.1% to 10% sucrose behenate by weight of the dietary fat.

* * * * *

UNITED STATES PATENT AND TRADEMARK OFFICE
CERTIFICATE OF CORRECTION

PATENT NO. : 7,695,971 B2
APPLICATION NO. : 10/567143
DATED : April 13, 2010
INVENTOR(S) : Ronald James Jandacek et al.

It is certified that error appears in the above-identified patent and that said Letters Patent is hereby corrected as shown below:

Column 11, line 63, Table B, bottom line, far-right column, delete "27.7 ± .6" and insert --27.7 ± 1.6--.

Column 15, line 27, Claim 4, insert a --.--, at the end of the Claim.

Column 15, line 30, Claim 5, insert a --.--, at the end of the Claim.

Signed and Sealed this
Twenty-fourth Day of April, 2012

David J. Kappos
*Director of the United States Patent and Trademark Office*